(12) United States Patent
Kreuzer et al.

(10) Patent No.: US 9,603,765 B2
(45) Date of Patent: *Mar. 28, 2017

(54) TELESCOPING AND ELEVATING FEMORAL SUPPORT

(71) Applicant: Innovative Orthopedic Technologies, LLC, Houston, TX (US)

(72) Inventors: Stefan Kreuzer, Houston, TX (US); Joseph W. Pieczynski, II, Austin, TX (US)

(73) Assignee: INNOVATIVE ORTHOPEDIC TECHNOLOGIES, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/427,555

(22) PCT Filed: Sep. 13, 2013

(86) PCT No.: PCT/US2013/059765
§ 371 (c)(1),
(2) Date: Mar. 11, 2015

(87) PCT Pub. No.: WO2014/043538
PCT Pub. Date: Mar. 20, 2014

(65) Prior Publication Data
US 2015/0238380 A1  Aug. 27, 2015

Related U.S. Application Data

(60) Provisional application No. 61/700,539, filed on Sep. 13, 2012.

(51) Int. Cl.
*A61G 13/12* (2006.01)
*A61B 6/04* (2006.01)
(Continued)

(52) U.S. Cl.
CPC ........ *A61G 13/1245* (2013.01); *A61B 6/0421* (2013.01); *A61G 13/0063* (2016.11);
(Continued)

(58) Field of Classification Search
CPC ...................................................... A61G 13/12
(Continued)

(56) References Cited

U.S. PATENT DOCUMENTS

| 4,526,355 A | 7/1985 | Moore et al. |
| 4,802,464 A | 2/1989 | Deprez |

(Continued)

FOREIGN PATENT DOCUMENTS

| WO | 2009/062324 A1 | 5/2009 |
| WO | 2009/126032 A1 | 10/2009 |
| WO | 2010/083301 A2 | 7/2010 |

OTHER PUBLICATIONS

PCT/US2013/059765 International Search Report and Written Opinion dated Dec. 16, 2013 (10 p.).

(Continued)

*Primary Examiner* — Fredrick Conley
(74) *Attorney, Agent, or Firm* — Conley Rose, P.C.

(57) ABSTRACT

A system for manipulating the position and orientation of a patient's leg includes an extension rail configured to be coupled to an operating table or bed. In addition, the system includes an elongate support rail coupled to the extension rail and having a longitudinal axis. Further, the system includes a deck coupled to the support rail. The deck is configured to be moved axially relative to the support rail.

16 Claims, 5 Drawing Sheets

(51) Int. Cl.
*A61G 13/00* (2006.01)
*A61B 6/00* (2006.01)
(52) U.S. Cl.
CPC ........ *A61G 13/0081* (2016.11); *A61G 13/125* (2013.01); *A61G 13/1295* (2013.01); *A61B 6/505* (2013.01)
(58) Field of Classification Search
USPC .............................................. 5/621–624, 648
See application file for complete search history.

(56) References Cited

U.S. PATENT DOCUMENTS

| | | | |
|---|---|---|---|
| 5,462,551 A * | 10/1995 | Bailey | A61G 13/12 606/88 |
| 5,645,079 A * | 7/1997 | Zahiri et al. | 5/610 |
| 6,058,534 A | 5/2000 | Navarro et al. | |
| 6,108,841 A * | 8/2000 | Cameron | A61G 13/0009 5/624 |
| 6,446,287 B2 * | 9/2002 | Borders | 5/618 |
| 2004/0133979 A1 | 7/2004 | Newkirk et al. | |
| 2007/0161935 A1 | 7/2007 | Torrie et al. | |
| 2010/0263129 A1 * | 10/2010 | Aboujaoude | A61F 5/3761 5/650 |
| 2012/0233782 A1 * | 9/2012 | Kreuzer | A61F 5/3761 5/624 |

OTHER PUBLICATIONS

PCT/US2013/059765 Informal Comments to Search Report and Written Opinion Dated Dec. 16, 2013; Response filed Mar. 12, 2014 (3 p.).

European Search Report dated Mar. 29, 2016, for European Application No. 13837517.5 (6 p.).

* cited by examiner

TELESCOPING AND ELEVATING FEMORAL SUPPORT

CROSS-REFERENCE TO RELATED APPLICATIONS

This application is a 35 U.S.C. §371 national stage application of PCT/US2013/059765 filed Sep. 13, 2013, and entitled "Telescoping and Elevating Femoral Support," which claims benefit of U.S. provisional patent application Ser. No. 61/700,539 filed Sep. 13, 2012, and entitled "Telescoping and Elevating Femoral Support," both of which are hereby incorporated herein by reference in their entirety.

STATEMENT REGARDING FEDERALLY SPONSORED RESEARCH OR DEVELOPMENT

Not applicable.

BACKGROUND

This invention relates generally devices and methods for supporting and manipulating a patient's leg and foot during surgery (e.g., hip joint surgery) or diagnostic procedure. More specifically, this invention relates to a devices and methods for guiding and applying fraction to a patient's leg during surgery or diagnostic procedure.

During surgery on a patient's leg (e.g., hip or knee surgery), certain positions and orientations of the leg may be preferred by the surgeon. For example, during one phase of hip surgery, the surgeon may want to place the patient's leg in tension (i.e., traction), whereas in another phase of hip surgery, the surgeon may want to rotate the patient's leg about a certain axis while maintaining traction. Moreover, in some cases, the surgeon may want to maintain traction or a particular rotational orientation of the patient's leg while adjusting the other. For example, during a hip replacement surgery, the patient typically lies on an operating table having a leg holding and support device attached thereto. The leg holding and support exerts tension on the patient's leg while holding the patient's leg in one or more desired positions to facilitate the surgery.

Some conventional leg holding and support devices enable traction to be applied to the patient's leg, but provide limited, if any, ability to simultaneously rotate the patient's leg about one or more axes. Other conventional leg holding and support devices enable rotation of the patient's leg about one or more axes, but do not provide the ability to independently control and adjust the rotation of the patient's leg about different axes. Still other conventional leg holding and support devices enable traction and rotation of the patient's leg about an axis simultaneously, but do not allow adjustment of one while maintaining the other.

Most conventional surgical tables designed for use in leg surgeries include a perineal post that is fixed to the table and positioned between the patient's legs against the perineum. The perineal post functions to maintain the patient's position on the surgical table while the patient's leg is pulled inferiorly (i.e., generally away from the patient's torso). This enables the application of inferior traction to the patient's leg by applying tension generally along the length of the leg. However, for some surgeries and diagnostic evaluations, it may be desirable to apply dorsal fraction to the femur to distract the hip joint ventrally. Although conventional surgical tables and associated traction devices enable the application of inferior traction, they provide very limited, if any, ability to controllably apply dorsal or ventral traction to the femur.

BRIEF SUMMARY OF THE DISCLOSURE

These and other needs in the art are addressed in one embodiment by a system for manipulating the position and orientation of a patient's leg. In an embodiment, the system comprises an elongate support rail coupled to the extension rail and having a longitudinal axis. In addition, the system comprises a deck coupled to the support rail. The deck is configured to be moved axially relative to the support rail.

These and other needs in the art are addressed in another embodiment by a system for manipulating the position and orientation of a patient's leg. In an embodiment, the system comprises an extension rail configured to be coupled to an operating table or bed. The extension rail has a distal end comprising a connector with a vertical throughbore. In addition, the system comprises an elongate support rail having a longitudinal axis, a first end, and a second end. Further, the system comprises a post pivotally coupled to the first end of the support rail. The support rail is configured to pivot about a horizontal axis relative to the post. The post is slidingly disposed in the throughbore of the connector.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
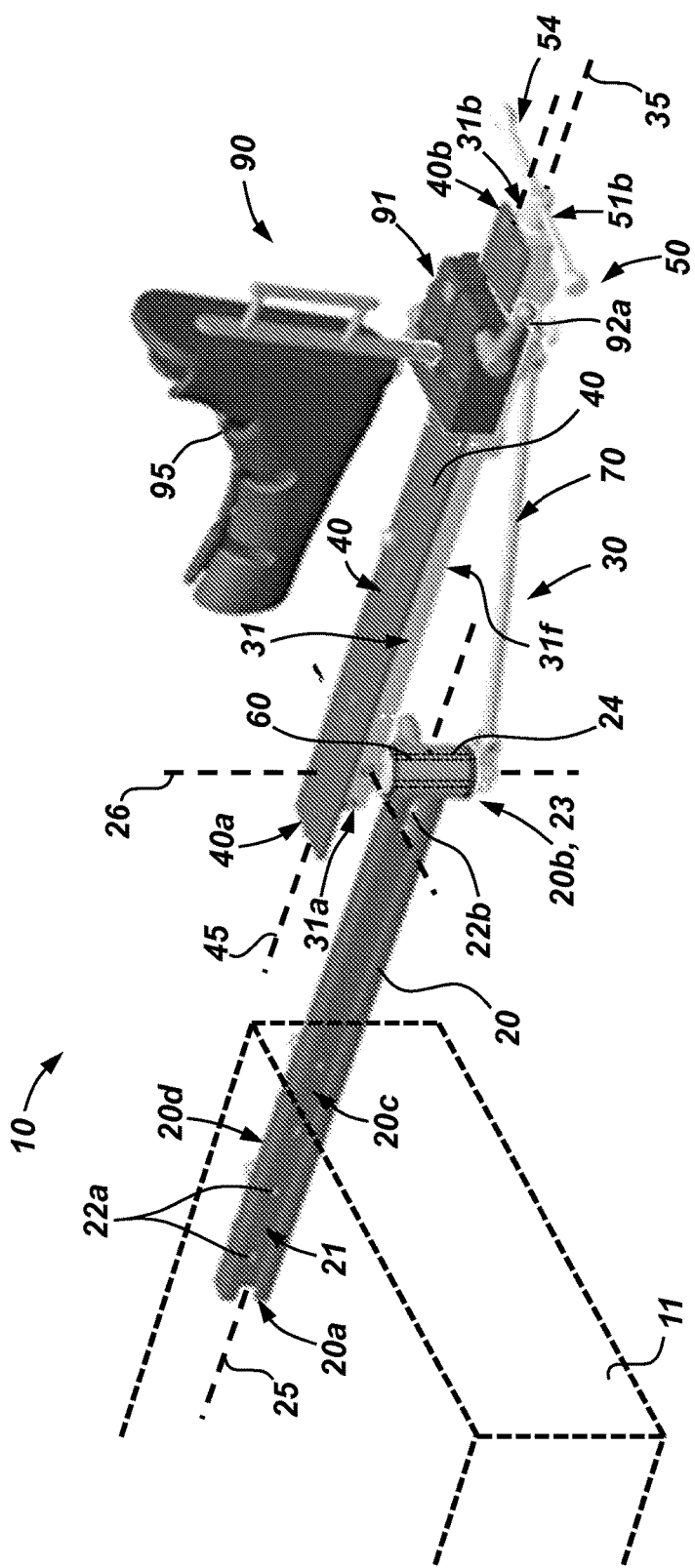
FIG. 1 is a perspective view of an embodiment of a system for supporting a patient's leg and foot during a medical procedure in accordance with the principles described herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms or phrases are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. Additionally, as used herein, the terms "bed" and "table" refer to a patient bed, operating table, an examination bed, or other medical bed or table used for medical procedures, operations, diagnostics, and care.

Figure 2:
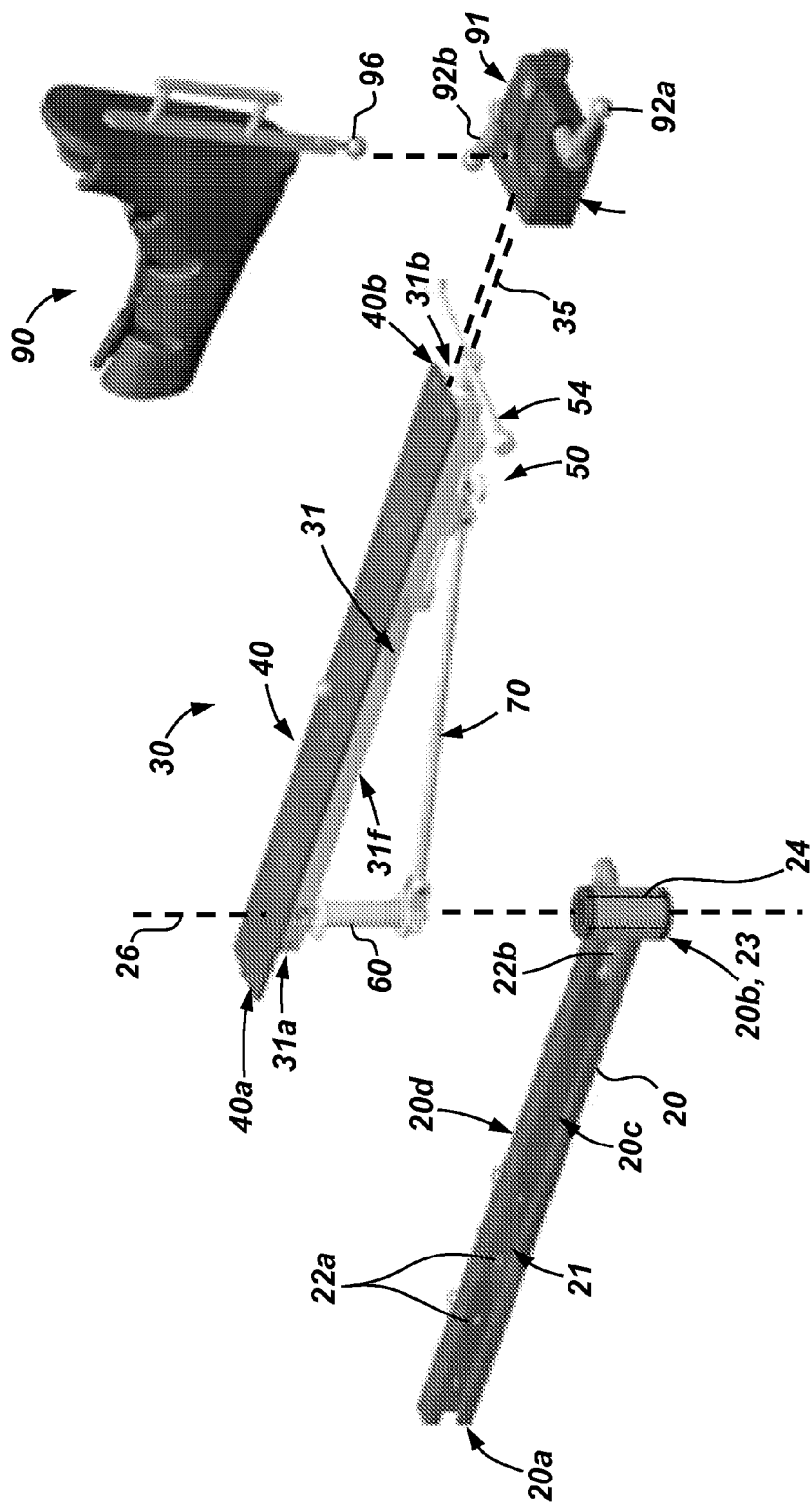
FIG. 2 is an exploded perspective view of the system of FIG. 1.
Figure 3:
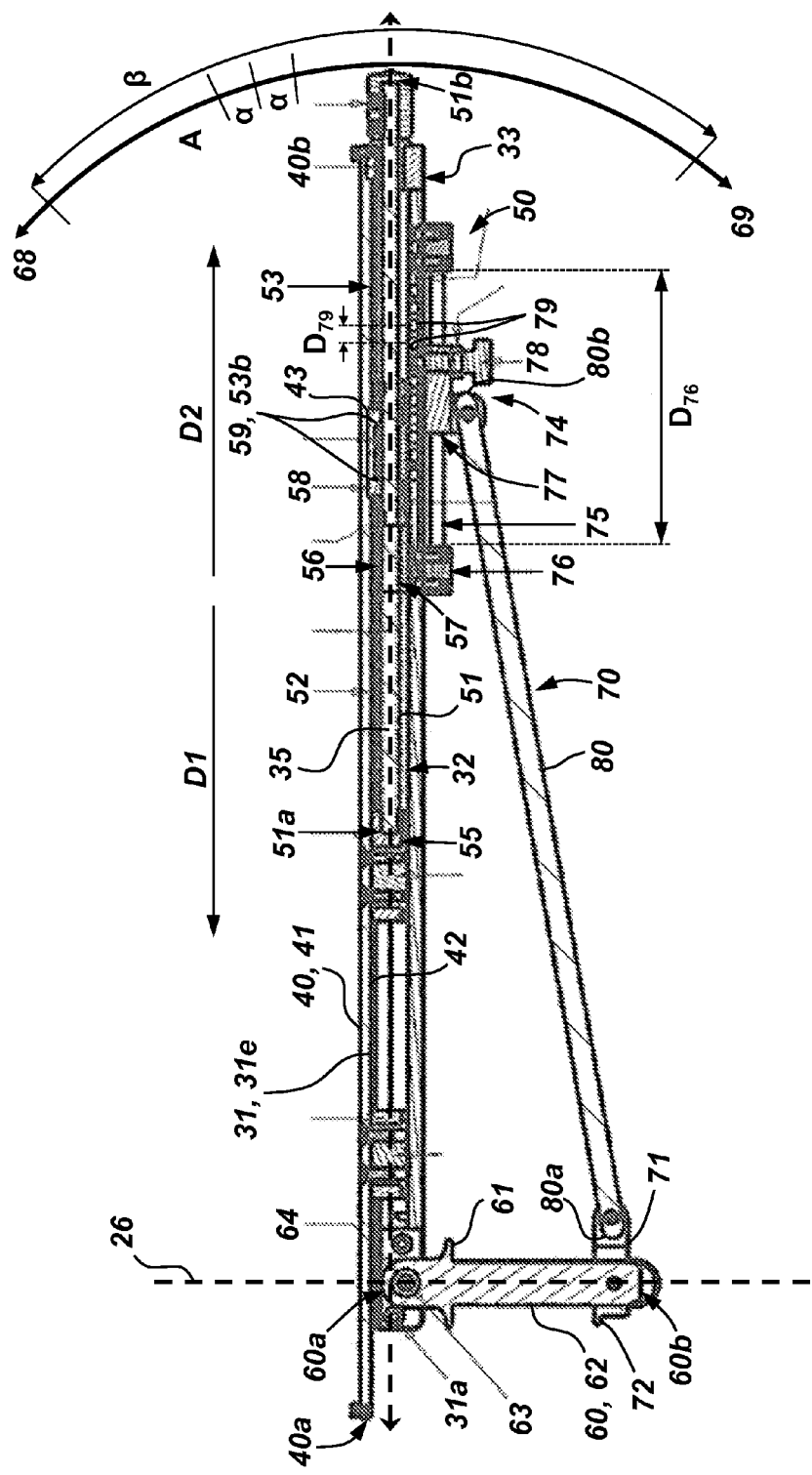
FIG. 3 is a cross-sectional side view of the leg positioning assembly of FIG. 1.
Figure 4:
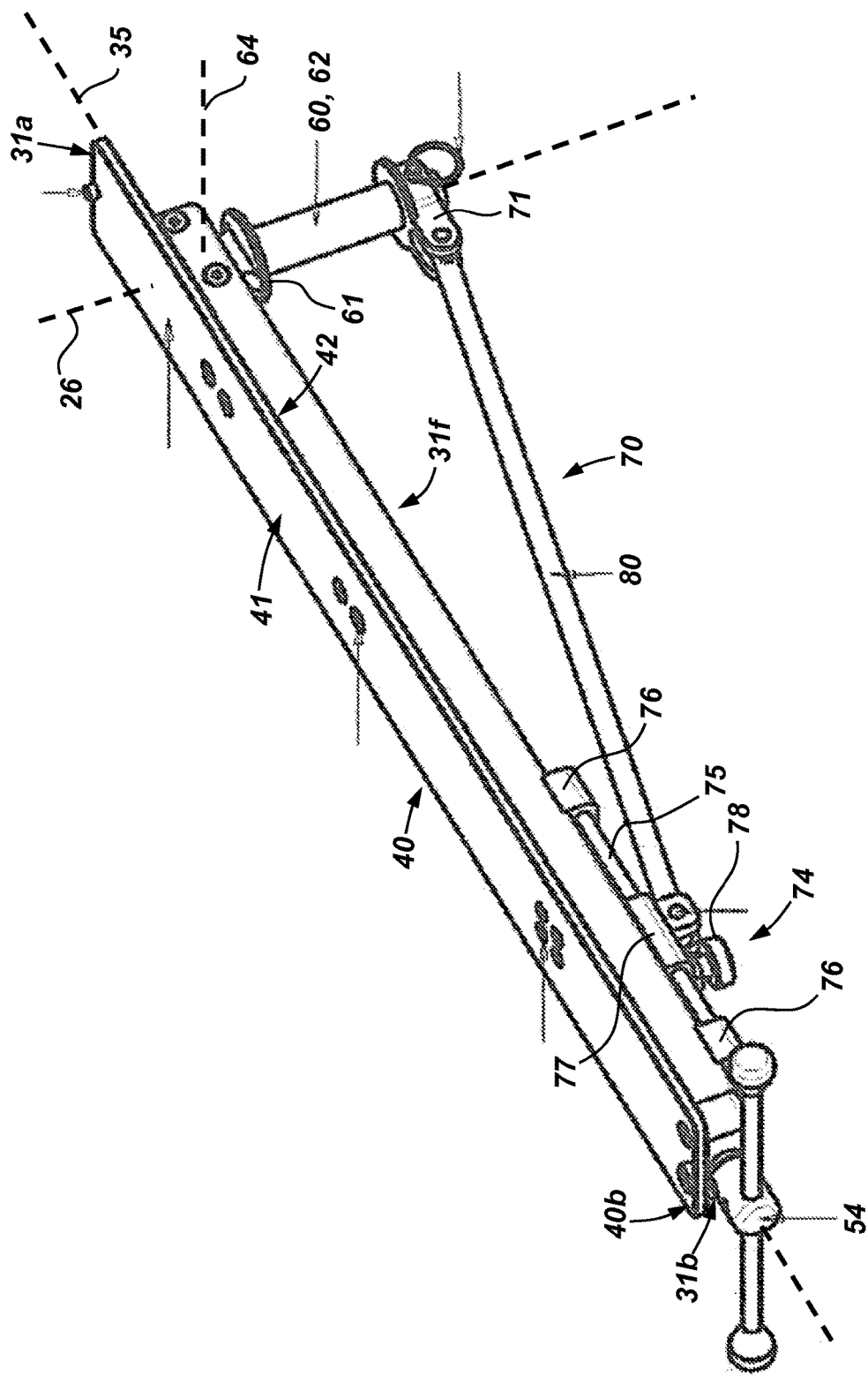
FIG. 4 is a perspective top view of the leg positioning assembly of FIG. 1.
Figure 5:
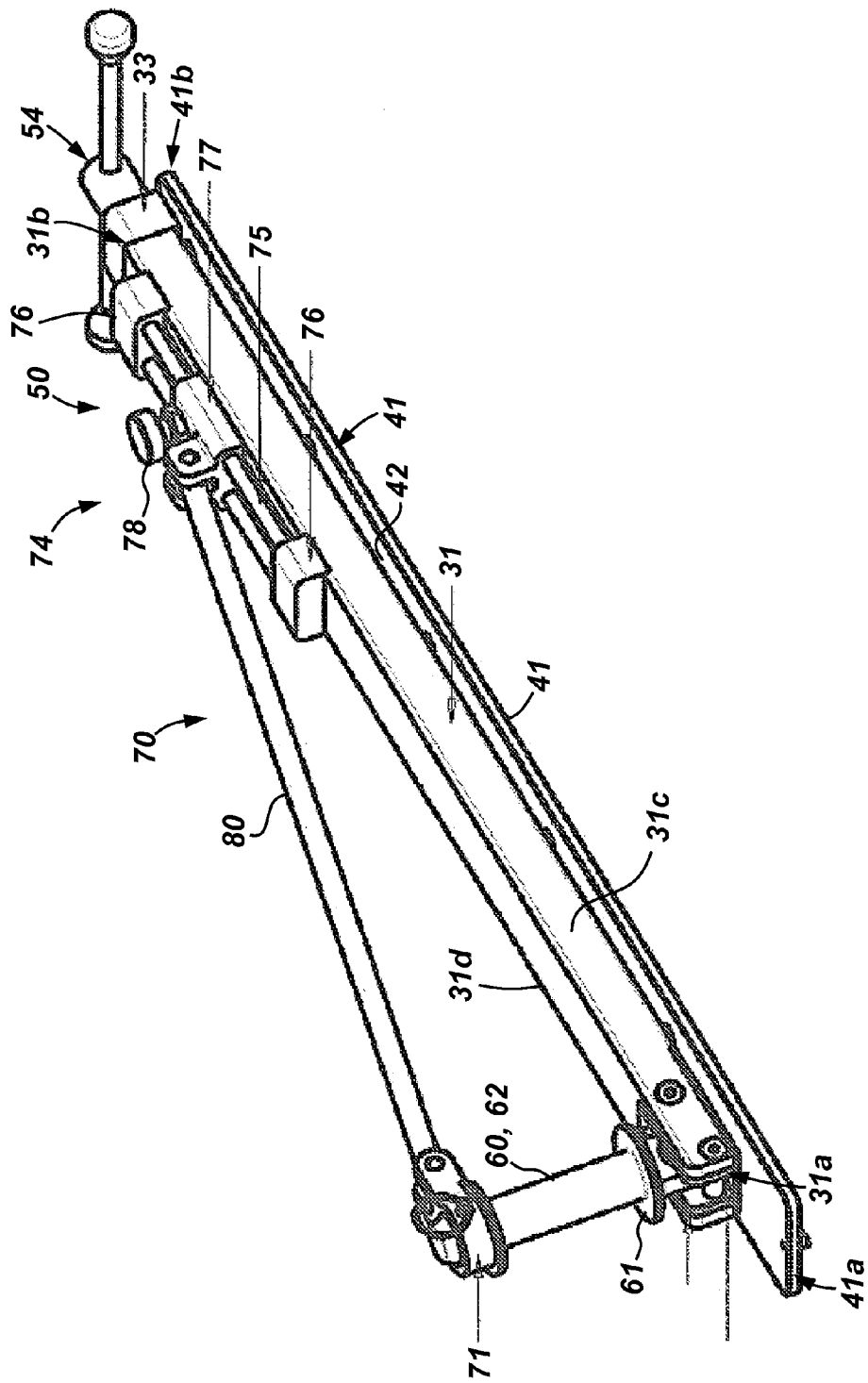
FIG. 5 is a perspective bottom view of the leg positioning assembly of FIG. 1.

Referring now to FIGS. 1 and 2, an embodiment of a system 10 for supporting and manipulating a patient's leg during a surgical or diagnostic procedure is shown. As will be described in more detail below, with one of the patient's feet and associate ankle removably secured to system 10, and system 10 can be used vary the position and orientation of the patient's corresponding leg, as well as controllably apply fraction to the patient's corresponding leg. In general, system 10 can be used to support and manipulate the patient's leg undergoing the procedure, referred to herein as the "affected" leg, or the patient's opposite leg (i.e., the patient's leg that is not the subject of the procedure), referred to herein as the "unaffected" leg.

In this embodiment, system 10 includes an extension rail 20 coupled to an operating table or bed 11 (shown in phantom in FIG. 1), a leg positioning assembly 30 pivotally coupled to extension rail 20, and a foot attachment assembly 90 moveably coupled to assembly 30. Extension rail 20 is an elongate rigid member having a central or longitudinal axis 25, a first or table end 20a, a second or distal end 20b, and inner lateral side 20c extending between ends 20a, 20b and facing table 11, and an outer lateral side 20d extending between ends 20a, 20b and facing away from table 11. A portion of rail 20 extending axially from end 20a is moveably coupled to the lateral side of table 11, and end 20b is axially spaced away from table 11. In general, rail 20 can be coupled to table 11 by any suitable means known in the art. In this embodiment, inner side 20c of rail 20 includes a C-shaped recess 21 extending axially from end 20a that slidingly engages a mating profile provided on an elongate rail on the side of table 11.

Distal end 20b of extension rail 20 comprises a connector 23 including a cylindrical throughbore 24 having a central axis 26. Axes 25, 26 intersect and are oriented orthogonal to each other. When extension rail 20 is coupled to bed 11, axis 25 of rail 20 is oriented horizontally and axis 26 of throughbore 24 is oriented vertically. As will be described in more detail below, leg positioning assembly 30 is coupled to extension rail 20 via connector 23, and further, assembly 30 is configured to pivot relative to extension rail 20 about axis 26.

A plurality of locking assemblies 22a are provided on extension rail 20 to releasably lock rail 20 to table 11, and a locking assembly 22b is provided at distal end 20b to releasably lock extension rail 20 to leg positioning assembly 30. More specifically, each locking assembly 22a has a locked position preventing rail 20 from moving axially relative to table 11 and an unlocked position allowing rail 20 to be moved axially relative to table 11. In addition, locking assembly 22b has a locked position preventing leg positioning assembly 30 from rotating relative to rail 20 about axis 26 and an unlocked position allowing leg positioning assembly 30 to rotate about axis 26 relative to extension rail 20. In this embodiment, each locking assembly 22a, 22b is manually transitioned between the locked and unlocked positions by rotating a lever to advance a bearing member into and out of engagement with the elongate rail of table 11 slidingly disposed in recess 21 and a rigid post 60 of assembly 30 slidingly disposed in throughbore 24, respectively.

Referring now to FIGS. 1-5, leg positioning assembly 30 includes a rigid elongate support rail 31, a deck 40 moveably coupled to support rail 31, post 60 pivotally coupled to support rail 31, and a bracing assembly 70 extending from post 60 to support rail 31. Support rail 31 has a central or longitudinal axis 35, a first or proximal end 31a, a second or distal end 31b extending axially between ends 31a, 31b, a pair of laterally spaced sidewalls 31c, 31d extending axially between ends 31a, 31b, an upper or top side 31e, and a lower or bottom side 31f. Top side 31e is open and bottom side 31f is closed, and thus, support rail 31 has a centrally C-shaped cross-section and an inner cavity 32 defined by a recess extending from top side 31e.

Deck 40 is an elongate rectangular plate having a central or longitudinal axis 45 oriented parallel to axis 35, a first or proximal end 40a, a second or distal end 40b, a planar upper or top side 41 facing away from support rail 31, and a planar lower or bottom side 42 slidingly engaging support rail 31. Deck 40 can be axially moved and positioned (relative to axes 35, 45) relative to support rail 31, as desired, with an actuation assembly 50.

Referring still to FIGS. 1-5, in this embodiment, actuation assembly 50 includes a shaft 51, a mounting block 55, a drive anchor 56, and a connection member 58. Shaft 51 extends through end 31b of support rail 31 into cavity 32 and has a central axis oriented parallel to axes 35, 45, a first end 51a disposed in cavity 32, a second end 51b extending from cavity 32, a first axial section 52 extending from end 51a, and a second axial section 53 extending axially from end 51b to section 52. First axial section 52 is externally threaded. A portion of second axial section 53 has a smooth cylindrical outer surface that slidingly engages a radial bearing 33 mounted to end 31b of rail 31. A handle 54 coupled to end 51b is employed to rotate shaft 51, in either direction, about its central axis.

Mounting block 55 is slidingly disposed in cavity 32 and fixably attached to deck 40. In this embodiment, block 55 is attached to deck 40 with a plurality of bolts. Thus, block 55 moves axially with deck 40 relative to support rail 31. First end 51a of shaft 51 is rotatably disposed in a mating recess provided in block 55. With block 55 disposed in cavity 32 and secured to deck 40, deck 40 is prevented from rotating and pivoting relative to support rail 31.

Drive anchor 56 is fixably attached to support rail 31 within cavity 32, and includes an internally threaded throughbore 57. Axial section 52 extends axially through bore 57 and threadably engages anchor 56. Connection member 58 couples shaft 51 to deck 40 and prevents shaft 51 from moving axially relative to deck 40, while simultaneously allowing shaft 51 to rotate relative to connection member 58 and deck 40. In this embodiment, connection member 58 is disposed about second axial section 53 and includes a pair of radially inner annular shoulders 59 that axially abut a pair of mating radially outer annular shoulders 53b provided on the outer surface of section 53. In addition, connection member 58 is seated in a mating recess 43 provided in bottom surface 42 of deck 40.

As previously described, anchor 56 is fixably attached to rail 31, shaft 51 threadably engages anchor 56, mounting block 55 is fixably attached to deck 40, and shaft 51 is prevented from moving axially relative to connection member 58 and deck 40. Further, shaft 51 can be rotated about its central axis relative to anchor 56, rail 31, connection member 58, mounting block 55, and deck 40. Thus, rotation of shaft 51 with handle 54 about its central axis in one direction causes shaft 51, connection member 58, deck 40, and mounting block 55 to move axially (relative to axes 35, 45) relative to support rail 31 in a first direction D1; and rotation of shaft 51 with handle 54 about its central axis in the opposite direction causes shaft 51, connection member 58, deck 40, and mounting block 55 to move axially (relative to axes 35, 45) relative to support rail 31 in a second direction D2.

Referring still to FIGS. 1-5, post 60 is coaxially disposed in throughbore 24. In other words, the central axis of post 60 is coaxially aligned with central axis 26. In addition, post 60 has a first or upper end 60a extending upwardly from connector 23, a second or lower end 60b extending downwardly from connector 23, and an annular flange 61 disposed between ends 60a, 60b proximal upper end 60a. The portion of post 60 within bore 24 has a cylindrical outer surface 62 that slidingly engages connector 23. Upper end 60a of post 60 is pivotally coupled to end 31a of support rail 31 with a pin 63 having a central axis 64 oriented orthogonal to axes 35, 26. Thus, support rail 31 can pivot about end 31a and axis 64 relative to post 60 and extension rail 20. With extension rail 20 mounted to table 11, axis 25 is horizontally oriented and axis 26 is vertically oriented as previously described, and further, axes 35, 45, 64 are horizontally oriented. Consequently, by pivoting support rail 31 about end 31a, end 30b of support rail 31 and end 40b of deck 40 can be moved up and down along arc A as represented by arrows 68, 69, respectively.

Bracing assembly 70 extends between post 60 and support rail 31, and provides support to the distal portion of support rail 31 while allowing support rail 31 and deck 41 to pivot up and down relative to post 60 and extension rail 20. In this embodiment, bracing assembly 70 includes a collar 71 disposed about lower end 60b of post 60, a slider assembly 74 coupled to support rail 31 proximal end 31b, and an extension or link rod 80 extending from collar 71 to assembly 74. Collar 71 is pinned to post 60, and thus, cannot move translationally or rotationally relative to post 60. In addition, the outer surface of collar 71 includes an annular flange 72 that axially abuts connector 23.

Slider assembly 74 includes a pair of laterally spaced parallel elongate guide or slide members 75 and a slide block 77 slidably mounted to guide members 75. Members 75 are oriented parallel to axes 35, 45 and are positioned below bottom side 31f of rail 31. The ends of guide members 75 are coupled to rail 31 with rigid mounts 76. Slide block 77 is free to move axially (relative to axes 35, 45) along guide members 75 between mounts 76, but is prevented from rotating relative to guide members 75. In addition, slide block 77 includes a locking member 78 for releasably locking slide block 77 to support rail 31. Namely, locking member 78 has a locked position preventing sliding member 77 from moving axially relative to guide members 75 and support rail 31, and an unlocked position allowing sliding member 77 to move axially relative to guide members 75 and support rail 31. When locking member 78 is locked, support rail 31 and deck 40 are prevented from pivoting relative to post 60.

In this embodiment, locking member 78 is a pull plunger biased to the locked position. In particular, the pull plunger extends through slide block 77 between guide members 75 and has an upper end 78a configured to engage one of a plurality of axially spaced receptacles 34 provided in an indexing plate 36 mounted to bottom side 31f of support rail 31. Locking member 78 is biased upward into engagement with bottom side 31f (e.g., with a spring), and thus, end 78a will be biased into the receptacle 79 it is aligned with. To unlock member 78, the pull plunger must be pulled downward out of the corresponding receptacle 79 to allow slide block 77 to slide along guide members 75.

Extension rod 80 is an elongate rigid member having a first or proximal end 80a pivotally coupled to collar 71 and a second or distal end 80b pivotally coupled to slide block 77. In this embodiment, extension rod 80 has a fixed length, however, in other embodiments, the extension rod (e.g., rod 80) is an extendable and retractable support. Still further, in other embodiments, the extension rod can be replaced with a linear actuator such as a hydraulic or pneumatic piston-cylinder assembly.

As previously described, locking member 78 has a locked position preventing sliding member 77 from moving axially relative to guide members 75 and support rail 31, and an unlocked position allowing sliding member 77 to move axially relative to guide members 75 and support rail 31. By unlocking member 78 and moving slide block 77 along guide members 75, support rail 31 and deck 40 can be pivoted (up or down) about axis 64 and through arc A. As support rail 31 pivots about axis 64 and slide block 77 moves along guide members 75, extension rod 80 pivots relative to collar 71 and slide block 77. Slide block 77 moves along guide members 75 until locking member 78 is biased into the next receptacle 79, which locks slide block 77 in place. Thus, the axial distance $D_{79}$ between adjacent receptacles 79 defines a pivot angle $\alpha$ along arc A through which support rail 31 and deck 40 can be rotated as locking member 78 moves between axially adjacent receptacles 79. In embodiments described herein the pivot angle $\alpha$ measured along arc A through which support rail 31 and deck 40 can be rotated as locking member 78 moves between axially adjacent receptacles 79 is preferably less than or equal to 10°. In some embodiments, the pivot angle $\alpha$ through which support rail 31 and deck 40 can be rotated as locking member 78 moves between axially adjacent receptacles 79 is 5°, or even as low as 1°. In general, the axial distance between receptacles 79 can be varied and customized as desired to achieve any desired pivot angle. In addition, the axial distance $D_{76}$ between mounts 76 also limits the maximum pivot angle $\beta$ along arc A through which support rail 31 and deck 40 can rotate as slide block 77 moves between mounts 76. In embodiments described herein, the axial distance between mounts 76 is preferably between 2.0 and 12.0 inches, and more preferably between 3.0 and 7.0 inches.

As described, the axial distance $D_{79}$ between receptacles 79 and the axial distance $D_{76}$ between mounts 76 determines the range of motion of support rail 31 and deck 40 along the arc A. In embodiments described herein, distances $D_{76}$, $D_{79}$ are preferably predetermined such support rail 31 and deck 40 can pivot upward about 60° from horizontal, about 45° above horizontal, and in certain configurations about 30° above horizontal. Further, in embodiments described herein, distances $D_{76}$, $D_{79}$ are preferably predetermined such support rail 31 and deck 40 can pivot downward about 45° from horizontal, about 35° below horizontal, and in certain configurations about 25° below horizontal.

In general, the components of system 10 can be constructed of any suitable material(s) including metals and metal alloys (e.g., steel, aluminum), non-metals (e.g., polymers), composites (e.g., carbon fiber and epoxy matrix composite), or combinations thereof. However, since system 10 is employed for surgical or diagnostic procedures, the components of system 10 are preferably constructed of material(s) that can be sterilized, for example by an autoclave. It should be appreciated that the components system 10 are modular, and thus, can be sterilized together or selectively in cases where select components are exposed during the procedure (i.e., not covered by sterile drapes) whereas other components are not exposed during the procedure (i.e., covered by sterile drapes). As is known in the art, sterile drapes are used to cover and isolate unsterilized equipment in an operating room. Components that are below the drape are not necessarily sterilized but, those that are positioned above the drape must be sterile to reduce the potential for infections. The modularity of system 10 also enables replacement of worn or damaged parts without having to replace the entirety of system 10.

System 10 is also reversible, meaning is can be used with the patient's left or right leg. Namely, extension rail 20 can be secured to a mating profile on either side of table 11, and further, positioning assembly 30 can be coupled to extension rail 20 via connector 23 and post 60 regardless of whether rail 20 is coupled to the left or right side of table 11.

Referring still to FIGS. 1-5, foot attachment assembly 90 includes a slide block 91 slidably mounted to deck 40 and a boot 95 coupled to slide block 91 with a ball and socket joint 96. Slide block 91 includes a pair of locking assemblies 92a, 92b. Locking assembly 92a has a locked position preventing slide block 91 from moving axially along deck 40 and an unlocked position allowing slide block 91 to move axially along deck 40. Locking assembly 92b has a locked position preventing boot 95 from pivoting relative to slide block 91 and an unlocked position allowing boot 95 to move omni-directionally relative to slide block 91. In this embodiment, each locking assembly 92a, 92b is manually transitioned between the locked and unlocked positions by rotating a lever to advance a bearing member into and out of engagement with the deck 40 and the ball of joint 96, respectively.

As previously described, system 10 allows the patient's leg supported by system 10 (affected or unaffected leg) to be manipulated and positioned as desired, while simultaneously applying traction to the patient's leg. In particular, the patient's foot of the leg to be supported with system 10 is secured within boot 95. The patient's leg can be manipulated and positioned as desired by pivoting boot 95 omni-directionally relative to slide block 91 and deck 40, moving slide block 91 along deck 40, moving deck 40 axially relative to support rail 31 and extension rail 20, pivoting deck 40 within arc A relative to extension rail 20, or combinations thereof. Any one or more of these movements to manipulate the leg can be selectively and independently performed, while others are locked or held in position. For example, lock 92a can be locked while deck 40 is moved axially and/or boot 95 is pivoted. As another example, locks 92a, 92b can be locked while deck 40 is moved axially and/or deck 40 is pivoted up or down. Tension can be applied to the patient's leg with system 10 in several different ways. Slide block 91 can be moved axially toward end 40b of deck 40 to apply traction, deck 40 can be moved axially along support rail 31 to apply traction, deck 40 can be pivoted through arc A to apply fraction, or combinations thereof.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A system for manipulating the position and orientation of a patient's leg, the system comprising:
   an extension rail configured to be coupled to an operating table or bed;
   an elongate support rail pivotally coupled to the extension rail, wherein the support rail has a longitudinal axis;
   a deck moveably coupled to the support rail;
   a foot attachment assembly moveably coupled to the deck, wherein the foot attachment assembly is configured to move axially along the longitudinal axis relative to the deck, wherein the foot attachment assembly includes a first slide block slidably mounted to the deck and a boot pivotally coupled to the first slide block; and
   an actuation assembly coupled to the deck and the support rail, wherein the actuation assembly is configured to controllably move the deck axially along the longitudinal axis relative to the support rail;
   a guide member coupled to the support rail, a second slide block slidably mounted to the guide member, a post pivotally coupled to the support rail, and an extension rod pivotally coupled to the post and the second slide block.

2. The system of claim 1, wherein the actuation assembly includes an operating handle rotatably positioned proximal an end of the deck that is distal the extension rail.

3. The system of claim 1, wherein the first slide block is configured to be releasably locked on to the deck.

4. The system of claim 1, wherein the actuation assembly comprises an externally threaded shaft, a drive anchor fixably attached to the support rail and threadably engaging the shaft, and a connection member coupling the shaft to the deck;
   wherein the shaft is configured to rotate relative to the drive anchor and the connection member;
   wherein the connection member is configured to prevent the shaft from moving axially relative to the deck.

5. A system for manipulating the position and orientation of a patient's leg, the system comprising:
an extension rail configured to be coupled to an operating table or bed;
an elongate, support rail pivotally coupled to the extension rail, wherein the support rail has a longitudinal axis;
a deck coupled to the support rail, wherein the deck is configured to be moved axially along the longitudinal axis relative to the support rail; and
a foot attachment assembly moveably coupled to the deck, wherein the foot attachment assembly is configured to move axially along the longitudinal axis relative to the deck, wherein the foot attachment assembly includes a first slide block slidably mounted to the deck and a boot pivotally coupled to the first slide block;
wherein the support rail and the deck are configured to pivot laterally relative to the extension rail about a vertical axis;
wherein the support rail and the deck are configured to pivot up and down relative to the extension rail about a horizontal axis, wherein the horizontal axis intersects the vertical axis and is oriented perpendicular to the vertical axis;
a guide member coupled to the support rail, a second slide block slidably mounted to the guide member, a post pivotally coupled to the support rail, and an extension rod pivotally coupled to the post and the second slide block.

6. The system of claim 5, wherein the support rail has a first end pivotally coupled to the extension rail and a second end distal the extension rail, wherein the support rail is configured to pivot about the vertical axis and the horizontal axis relative to the extension rail at the first end.

7. The system of claim 5, wherein the second slide block includes a pull plunger;
wherein support rail includes a plurality of axially spaced receptacles configured to removably receive the pull plunger;
wherein the pull plunger is biased into engagement with one of the receptacles.

8. The system of claim 5, further comprising an actuation assembly configured to controllably move the deck axially along the longitudinal axis relative to the support rail.

9. A system for manipulating the position and orientation of a patient's leg, the system comprising:
an extension rail configured to be coupled to an operating table or bed, wherein the extension rail has a distal end comprising a connector with a vertical throughbore;
an elongate support rail having a longitudinal axis, a first end, and a second end;
a post pivotally coupled to the first end of the support rail, wherein the support rail is configured to pivot about a horizontal axis relative to the post, wherein the post is slidingly disposed in the throughbore of the connector;
a deck coupled to the support rail with an actuation assembly configured to move the deck axially relative to the support rail.

10. The system of claim 9, wherein the actuation assembly comprises an externally threaded shaft, a drive anchor fixably attached to the support rail and threadably engaging the shaft, and a connection member coupling the shaft to the deck;
wherein the shaft is configured to rotate relative to the drive anchor and the connection member;
wherein the connection member is configured to prevent the shaft from moving axially relative to the deck.

11. The system of claim 9, further comprising a guide member coupled to the support rail, a slide block slidably mounted to the guide member, a collar disposed about the post, and an extension rod having a first end pivotally coupled to the collar and a second end pivotally coupled to the slide block.

12. The system of claim 11, wherein the slide block has a lock configured to releasably lock the axial position of the slide block relative to the support rail.

13. The system of claim 12, wherein the lock is a pull plunger biased toward the support rail.

14. The system of claim 13, wherein the support rail includes a plurality of axially spaced receptacles configured to receive the pull plunger.

15. The system of claim 14, wherein each pair of axially adjacent receptacles are axially spaced apart by an axial distance D;
wherein the support rail is configured to pivot about the horizontal axis relative to the post through a pivot angle a when the slide block is moved axially the axial distance D;
wherein the pivot angle α is less than 10°.

16. The system of claim 11, wherein the guide member has a first end coupled to the support rail with a first mount and a second end coupled to the support rail with a second mount;
wherein an axial distance between the first mount and the second mount is between 2.0 in and 12.0 in.

* * * * *